US007385105B2

(12) United States Patent
Medrano et al.

(10) Patent No.: US 7,385,105 B2
(45) Date of Patent: Jun. 10, 2008

(54) ROOT ACTIVE PROMOTERS AND USES THEREOF

(75) Inventors: Leonard Medrano, Azusa, CA (US); Kenneth Feldmann, Newbury Park, CA (US); Tatiana Tatarinova, Los Angeles, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/305,589

(22) Filed: Dec. 16, 2005

(65) Prior Publication Data

US 2006/0143735 A1   Jun. 29, 2006

Related U.S. Application Data

(60) Provisional application No. 60/637,140, filed on Dec. 16, 2004.

(51) Int. Cl.
*A01H 5/00* (2006.01)
*C12N 15/82* (2006.01)
*C07H 21/04* (2006.01)

(52) U.S. Cl. .................. 800/295; 536/24.1; 435/419; 435/320.1

(58) Field of Classification Search ............... None
See application file for complete search history.

(56) References Cited

U.S. PATENT DOCUMENTS 5,459,252 A   10/1995   Conkling et al.

5,837,848 A   11/1998   Ely et al.
2006/0143735 A1*   6/2006   Medrano et al. ............ 800/279

FOREIGN PATENT DOCUMENTS

WO   WO 00/29566   5/2000
WO   WO 2004/013169   2/2004

OTHER PUBLICATIONS

Kim et al. (Plant Molecular Biology, 24:105-117, 1994).*
Bevan et al. (NCBI, GenBank, Sequence Accession No. AL035526, Published Mar. 25, 1999).*
Nitz I et al., "PYK 10, A seedling and root specific gene and promoter from *Arabidopsis thaliana*" Plant Science, 161 (2001), pp. 337-346.
Database EMBL [Online] Print Out, "*Arabidopsis thaliana* BAC F9D12." Jul. 17, 1998. Database Accession No. AF077407. XP002381460.
Database EMBL [Online] Print Out, "*Arabidopsis thaliana* BAC T19G15, from chromosome V near 60.5 cM, complete sequence." Nov. 16, 1998. Accession No. Ac005965. XP002381461.

* cited by examiner

*Primary Examiner*—David H. Kruse
*Assistant Examiner*—Vinod Kumar
(74) *Attorney, Agent, or Firm*—Birch Stewart Kolasch & Birch LLP

(57) ABSTRACT

The present invention is directed to root active promoter sequences, polynucleotide constructs comprising the root active promoters and methods of identifying the root active promoters, or fragments thereof. The invention further relates to the use of the present root active promoters to modulate transcript levels.

8 Claims, No Drawings

SEQUENCE LISTING

```
<160> NUMBER OF SEQ ID NOS: 7

<210> SEQ ID NO 1
<211> LENGTH: 734
<212> TYPE: DNA
<213> ORGANISM: Arabidopsis thaliana
<220> FEATURE:
<221> NAME/KEY: misc_feature
<222> LOCATION: (1)..(734)
<223> OTHER INFORMATION: Construct PT0839 from Report Number 239

<400> SEQUENCE: 1
aactcctagc ctaaaactaa aacacagttg atgactaatt ggtggagaac cattaaaaaa      60
aaaaaaaaaa gacagagtag actaacgaaa ccacaccttt acattttttct atttatctca     120 ccttcctaaa taaaaaatat ttattttaaa caaaaacaca ttttctgtac agacgtgggt     180
ttcgtaatgt ccataagtcc atccgtagtc taccatataa tttaacatct acttctctcc     240
agtggacgca aaagcttcga attgaatgtg ggcgttgctt ctctcgtgtc taatataaaa     300
```

```
tttggataat catgaattct tcgatgatag tgatataccg ttgacactga gtagttcatt    360
gcaataagta agatcttgtt tttgctaaaa agattcaatc atattttgaa cacttgccac    420
ccaccacttc caaaacttcc acaaattcat agatatagta atacacaggt tacttgacaa    480
aaggaataaa agtacaatat gatgctttac acattctcag tcaaaaaaaa cgataaaatg    540
aatgtgtaag ataatattgt ttaaaaaaga aaaaagaac aaaaaaaaga taatattgtt     600
ttcccgacga ctaatccaca ttcagtattt tataaaataa ctgaactcaa gttgctcgat    660
caaacaagta cccttaaatg tctctctgtc tatataaatg tacactcttc ccaaacaaaa    720
ccatatctca aaat                                                     734
```

```
<210> SEQ ID NO 2
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Construct PT0758 from Report Number 243

<400> SEQUENCE: 2
agctagccac atcagtgacc aaaaaagata attaacaaac caaataaaat aacaaatttt     60
gatcatttgg aataaaattt ataaaaggaa cgaaagcgcc ttctcacggg tcccatccat    120
tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgatttta    480
aatattagtt tttgttgtaa agagatcatt atatatgtct gtaatatttt tatactgagt    540
tacatgatat ttagttatta tagcgtaatt aactaagata agaaattaac taagtgata    600 ttctgattat tattattttt gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt    780
ttcgcatgaa aatatgaaag gagagaaatt tattattgtc acttatatat atatacatcg    840
taatcatttt ttcgtgaata attctctctc ccattccatt atttctcagt atctctcttt    900 ctttcccta ctttattgtt gcttttaaac cttcaatttg ctcataaacc aaatatataa    960
tatcaaaaca aacaaacaaa aaatcagaat tcccctaata                        1000
```

```
<210> SEQ ID NO 3
<211> LENGTH: 360
<212> TYPE: DNA
<213> ORGANISM: Arabidopsis thaliana
<220> FEATURE:
<221> NAME/KEY: misc_feature
<222> LOCATION: (1)..(360)
<223> OTHER INFORMATION: Construct PT0888 from Report Number 244

<400> SEQUENCE: 3
tgactttgta aggacaatta ccaaaagaga tttaaaaagg acacaacaac gaagatttgg     60
tcaactttag gttcataatc ataatgccac caacaaaaat tctttcacat ttttgtgaaa    120
```

```
ttgtgaaagc caatataaac atttcctgtt ttaaatttttt ttatgaaata aaactcataa        180
tgttaacgaa atgaattatt aaatgattga gaccataaat ggaccgcacg tatagtagtg        240
cccttccaca catgtaacgt aatcttctcc tcaaccaaaa agtctaaatt catattatat        300
atacacgaag actttcttac atcaaagaag cacaatctga aaatcatcga atccaaaata        360
```

<210> SEQ ID NO 4
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Construct PT0803 from Report Number 248

<400> SEQUENCE: 4

```
taatctaagt ttgcattcga tatttgcagg atttgcttca acactataac atggcctgca         60
agttttgata gattccaaga aatttgtttc atttcatcgc tgtattttgc agtttgtcct        120
agaagttgga gatatcgaga aaaaacacaa acccttgctt tcttctaagg gctagtttgt        180
tctgtttacc taatacaatt gtcatattca attgatgatt ccgttacctt taacactttg        240
cctggaaata aactactcat tatgcttcat ggtttccatt acctctctgc cagtgaatct        300
gacttaaagc tatttaatct cgttcattaa tgttcatgat tgaaattgaa tcactattgg        360
tgaattatgt ttagaaattg aatcagaccc ttgttttctt ctaacatcta aggcctactt        420
tgttcttttt gtttatacat ttatcatctt aaattggtaa tctcgttact ttagcacttc        480
tggcctacaa ataaactact cattatgctg aaattgtttg agttccctta ccaaaaccaa        540
ttaagatact gtttatagta aagaaaaagt gattgaaaca gttctgactt tcttgtaatt        600
ttgtagtcgg aatcatgcga tgtttattgg ttccaccaac tatgcactgt caagtgtcaa        660
ccaccaaata cactatacta gagacttaac cattagaaat tggttcttca aattggccat        720
ataaattata aatccatgaa ctgactaaaa agactcatcg ttgcttttg  tgaagtgtta        780 aaccaaatga tcacggatat aaattagaat aattgcgaca cagatctacc agcaatttcg        840
accgttgcaa caaagccatg attcaaaaag tttgctttt  taatcttacc gttggctcct        900
agcaactgca aatccttaag atcaacatct ccttcttaat tcttacccag ttattgaatt        960
ttctgaaact atcgttcttg atcttaaaag ctcaacaaaa                             1000
```

<210> SEQ ID NO 5
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Construct PT0779 from Report Number 249

<400> SEQUENCE: 5

```
tcaattttgg attttgttat ttgctattca aaatcattaa agataaatttg gtcttaataa         60 tcttctaaac tttatatgat ctgattgaat ctaaaccgtt caataaaatt aattcccttc        120
aatctaaacc gttcaacaaa ataagtgaa  ataatttat  tttttttatct tcactttaaa       180 gacatataat tataaataac ataattcata tggtctttat tttgccaaaa agtgtataa         240 cctgtcaaat agttaaaaaa aacacttata atcataaaaa atattatacc aattttgtga        300
atcttacatt tttgtaaata ttttactttc actaaaatta catacacatt tttaaacaca        360
ttttaacaca tttatcttat cactaaataa caacaaaaaa aaatcccaat tattatttaa        420
```

| | |
|---|---|
| ttatgtttga ttaaaaaatt tatatttata aatttaaaat atcaaattta ttcaaatatt | 480 |
| tagtataaaa acccaaataa accgattgtc cgcggtttac cgcggattaa atcctagtta | 540 |
| ttattattgc gattcccttt ccccatgctc tgaaatttgt taatcatttg tccctatttc | 600 |
| tgcttaacca cttacatttc ataattttg agtttatatt gtttaatgta tatattttac | 660 |
| actattactt tcattactta atagtcagaa atctcatacc ataatcatta cgatacaaaa | 720 |
| tcatagtcca attattttct tcattactga cttttcggc tcttttacaa aaagctaata | 780 |
| tctttatcta cagttgatca tattttaatt ttcaccaaaa gtaaattaa acagaagact | 840 |
| ctaatcatat cagtgatcaa agtgggccaa catgggccca tacacgccac aaagaaccca | 900 |
| acccaaaagt ccaaagatat tctttaagct cagtttataa attgcattct ctttctcctt | 960 |
| cctacaggcc aacccaacat caacgactta ttcgagaga | 999 |

```
<210> SEQ ID NO 6
<211> LENGTH: 763
<212> TYPE: DNA
<213> ORGANISM: Arabidopsis thaliana
<220> FEATURE:
<221> NAME/KEY: misc_feature
<222> LOCATION: (1)..(763)
<223> OTHER INFORMATION: Construct PT0837 from Report Number 250

<400> SEQUENCE: 6
```

| | |
|---|---|
| aactacaagg gagacataat atcaccatct ggttcctgtt atcatctgaa gatttcttgt | 60 |
| tttaccttcc agtgataaaa tgatccttat aatacatata gatatattaa attgctgtat | 120 |
| tttaagatta tagatatata aggtacatga gagtgtttat ttaaaaaaat tcacttggaa | 180 |
| ttcatgttt gtgatacgtt agattggaat ccatttggga aaagaagaat catctgttct | 240 |
| tatgtctcaa attttgactt cattcacttt tcttcttgtc ttttaagaaa gcttccacaa | 300 |
| tctaactgtt cgatgtgaaa actgagattc gagtaagaaa atgtgaactg tgttatactg | 360 |
| tttttaatt agataattta gattgcactc agataaatta ataacattcc tcgaatactt | 420 |
| ttatgtgatt ggatatatta ggtatatctg ccaaccaacc aataaactgc tatgtttaaa | 480 |
| caaattaaat aaattagtat atgtttactc aagaataaag aagatagaaa agaaaattct | 540 |
| atatgagcta aatttgctgg aggaggcatc ggacgtgggt accagacctt tccaagcaca | 600 |
| cgagtagtgc ttagccatgt catgctaaca tacaccattt ggttcataca aaatccaaat | 660 |
| caaaatctat ttttaaaatc ttttgcacac gtctttgaaa aacacctctc atactatagc | 720 |
| tacggaagct tcaatttcaa ggtttgtcta aaagctaacg att | 763 |

```
<210> SEQ ID NO 7
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Construct PT0818 from Report Number 251

<400> SEQUENCE: 7
```

| | |
|---|---|
| aatgatgtat taactctgta aattaagata acgttcttg tattttatat gtcattttaa | 60 |
| gaaagtattt tatatatgat ttgtattcat tttaagaagt atacgaagag agtttgattt | 120 |
| tattttcctc gtgacgaaat ttgtttctga taaatttgaa agatatgatt tattttctgt | 180 |
| cttggtaagg tcagttatca cattaaagac taaatagtaa attttatgtt ttttgtttc | 240 |

```
tgaattattt cagaatttct tgttttattc atttaatatt taataatata tgttaaatga      300
tactattaca ctttagaaaa atgtgcttat ttctatcgta ccaaacttct cttttttac      360 cgaacttgtt actgtttgtt ttgtgaacga tttttgttta taaaaacatt actcgtttgt    420
gataaattta acacattttt gcataaaaat gtatcaatca tatacaaatg aaacattaca    480
tttttagtca tttttagtca ataagtagac gtgtgtatca tgattagttg atttaatcat    540
aattatgata tttaaaataa acatagttta atgttattat gttggttttt aatattttta    600
attaacgtca acctatttt tttatttt ttttacatat aactatgttg ttatggaagt      660
cactattaat ttaactgata aaatatacaa taaaatagaa aaaacaatag attttaataa    720
aagaataaaa aatttgaaga tacaaaaaca gttccttttt cttaataaat caaaatcaaa    780
gagatagtgt actgaagtga agagccagcc actatacgac atacgtatgt aattacgttt    840
taataacctg atggcaaata ataatatatt ttcgtcaaaa taaaatggtc gtatctcttt    900
gctaaaacca aaatgtcatg atgtgattac tcaattttct actataaata gattaccaaa    960
tcattcgatc ggagacaatc accaaagaaa gaagtacaaa                          1000
```

US 7,385,105 B2

ROOT ACTIVE PROMOTERS AND USES THEREOF

CROSS-REFERENCE TO RELATED APPLICATION

This Non-provisional application claims priority under 35 U.S.C. § 119(e) on U.S. Provisional Application No(s). 60/637,140 filed on Dec. 16, 2004, the entire contents of which are hereby incorporated by reference.

FIELD OF THE INVENTION

The present invention relates to root active promoters that are useful for modulating transcription of a desired polynucleotide. Such root active promoters can be included in a polynucleotide construct, expression cassette or vector, or inserted into the chromosome or used as an exogenous element to modulate in vivo and in vitro transcription of a polynucleotide. The invention also includes host cells and organisms, including plant cells and regenerated plants therefrom, with desired traits or characteristics obtained using polynucleotides comprising the root active promoters of the present invention.

BACKGROUND OF THE INVENTION

The economic value of roots arise not only from harvested roots, but also from the ability of roots to alter the soil in which they grow and to funnel nutrients to support growth and increase vegetative material, seeds, fruits, etc.

Roots have four main functions. First, they anchor the plant in the soil. Second, they facilitate and regulate the molecular signals and molecular traffic between the plant, soil and soil fauna. Third, the root provides a plant with nutrients gained from the soil or growth medium. Fourth, they condition local soil chemical and physical properties.

Roots arise from meristems cells that are protected by a root cap during root elongation, but as the root grows out, the cap cells abscise and the remaining cells differentiate to the tip. Depending on the plant species, some surface cells of roots can develop into root hairs. Some roots persist for the life of the plant, others gradually shorten as the ends slowly die back and some may cease to function altogether due to external influences.

Because plants are sessile organisms, their survival is critically dependent on rapid adaptation to environmental changes. In the soil, change can arise from alteration of the concentration of oxygen or carbon dioxide, nutrient availability, the presence (or absence) of microorganisms and overall soil humidity. For example, oxygen levels in the rhizosphere decrease rapidly during flooding. Hypoxic or anoxic conditions occur in submerged plant tissues and can have lasting effects on the subsequent growth and/or development of the plant.

Roots are also the sites of intense chemical and biological activities and as a result can strongly modify the soil they contact. For example, roots secrete a wide variety of high and low molecular weight molecules into the rhizosphere in response to biotic and abiotic stresses. They are also capable of absorbing toxic substances from the soil and then storing or modifying the toxins, resulting in soil improvement.

Roots coat themselves with surfactants and mucilage to facilitate these types of activities. Specifically, roots attract and interact with beneficial microfauna and flora that help to mitigate the effects of toxic chemicals, pathogens and stress in addition to facilitating water and nutrient assimilation and mobilization. Nutrients can take the form of ions and organic and inorganic compounds. Uptake of nutrients by roots produces a "source-sink" effect in a plant. The greater the source of nutrients, the larger "sinks" (such as stems, leaves, flowers, seeds, fruits, etc.) can grow.

Some plants, notably the Leguminous species, are capable of forming symbiotic associations in response to soil organisms. The *rhizobia* bacteria are examples of such a specific association. Here, the interaction between bacteria and the plant root results in the formation of a specific root structure, or nodule, in which nitrogen fixation is carried out. This symbiotic interaction provides a source of nitrogen for the plant that may not have been otherwise available.

Currently there is only limited ability to improve (1) plant nutrient uptake, (2) response to varying water conditions, (3) interaction with the soil environment (4) tolerance to pests that attack roots, including insects, fungi, bacteria, viruses, or nematodes and (5) the nutritional composition of roots for human food or animal feed applications. Thus a need exists for nucleic acid sequences that are able to drive transcription of desired genes in roots.

SUMMARY OF THE INVENTION

The present invention is directed to isolated polynucleotide sequences that comprise root active promoters from *Arabidopsis thaliana* used alone or in combination with other promoters, promoter control elements and motifs functional in plants.

It is an object of the present invention to provide isolated polynucleotides that are root active promoter sequences. These promoter sequences comprise, for example,
 (1) a polynucleotide having a nucleotide sequence according to any one of the promoter sequences set forth in Table 1 (SEQ ID NOs: 1-7) or a functional fragment thereof;
 (2) a polynucleotide having a nucleotide sequence with at least 80% sequence identity to any one of the promoter sequences set forth in Table 1 (SEQ ID NOs: 1-7) or a functional fragment thereof; and
 (3) a polynucleotide having a nucleotide sequence which hybridizes to any one of the promoter sequences set forth in Table 1 (SEQ ID NOs: 1-7) under a condition establishing at least a Tm-20° C.

Root-active promoters drive transcription in root tissue, e.g., root endodermis, root epidermis, or root vascular tissues. In some embodiments, root-active promoters are root-preferential promoters, i.e., drive transcription only or predominantly in root tissue.

In another embodiment, the present root active promoters are capable of serving as or fulfilling the function of a core promoter, an initiator site, a transcription factor binding site, an enhancer, an inverted repeat, a locus control region, or a scaffold/matrix attachment region.

In another embodiment, the present isolated polynucleotides comprise a root active promoter as described above, wherein the promoter is operably linked to a polynucleotide to be transcribed.

In another embodiment of the present invention, the root active promoters of the instant invention are operably linked to a heterologous polynucleotide that is a coding sequence or that is a regulatory sequence.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be from different species.

It is another object of the present invention to provide a host cell comprising an isolated polynucleotide or vector as described above or fragment thereof. Host cells include bacterial, yeast, insect, mammalian and plant. Such a root active promoter can modulate transcription of a sequence in cis- and/or in trans-.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free transcription system or a host cell. This method comprises providing a polynucleotide or vector according to the present invention as described above and contacting the sample of the polynucleotide or vector with conditions that permit transcription.

In another embodiment of the present method, the polynucleotide or vector preferentially modulates root growth, tolerance to pests, and soil interactions.

In another embodiment of the present method, the polynucleotide or vector preferentially modulates root composition for human food or animal feed applications.

The present invention also provides a method of obtaining an enhanced plant with a root active promoter selected from Table 1 (SEQ ID NOs: 1-7).

The present invention also provides an enhanced plant with a root active promoter selected from Table 1 (SEQ ID NOs: 1-7).

Other and further objects of the present invention will be made clear or become apparent from the following description.

DETAILED DESCRIPTION OF THE INVENTION

1. Definitions

Functionally Comparable Proteins or Functional Homologs: This term describes those proteins that have at least one functional characteristic in common. Such characteristics include sequence similarity, biochemical activity, transcriptional pattern similarity and phenotypic activity. Typically, the functionally comparable proteins share some sequence similarity or at least one biochemical property. Within this definition, homologs, orthologs and analogs are considered to be functionally comparable. In addition, functionally comparable proteins generally share at least one biochemical and/or phenotypic activity.

Functional homologs will give rise to the same characteristic to a similar protein, but not necessarily to the same, degree. Typically, functional homologs give the same characteristics where the percent sequence identity of one of the comparables is at least 20% of the other; more typically, between 30 to 40%; even more typically, between 50%-60%; even more typically 70% to 80%; even more typically between 90% to 100% of the other.

Functionally Comparable Promoters or Functionally Similar Promoters: As used herein, "Functionally Comparable Promoters" or "Functionally Similar Promoters" are promoters that drive genes encoding functional homologs having similar expression patterns. Functionally comparable promoters may share sequence identity. Functionally comparable promoters may be isolated from the same plant species or different plant species. Such promoters include both naturally occurring promoters and non-natural promoter sequences. Non-natural functionally similar promoters include synthetic or modified natural promoters with nucleotide substitutions, insertions, deletions or fragments of naturally-occurring promoter sequences that do not substantially affect transcription modulation activity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Percentage of sequence identity: As used herein, the term "percent sequence identity" refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

In case of the functional homolog searches, to ensure a subject sequence having the same function as the query sequence, the alignment has to be along at least 80% of the length of the query sequence so that the majority of the query sequence is covered by the subject sequence. To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Root-active Promoters: Root-active promoters drive transcription in root tissue, e.g., root endodermis, root epidermis, or root vascular tissues. Thus, in the present application, the terms "root active", "root active, and "root preferential" are intended to be interchangeable unless combined with/ followed by additional terminology to distinguish between the three terms.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% \ G+C)-(600/N) \tag{1}$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log \{[Na^+]/(1+0.7[Na^+])\}+0.41(\% \ G+C)-500/L \ 0.63(\% \ \text{formamide}) \tag{2}$$

where L is the length of the probe in the hybrid. (P. Tijessen, "Hybridization with Nucleic Acid Probes" In Laboratory Techniques in Biochemistry and Molecular Biology, vand der Vliet, ed., c. 1993 by Elsevier, Amsterdam, which is hereby incorporated by reference in its entirety). The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al. (1973) J. Mol. Biol. 81:123), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

TATA to start: "TATA to start" shall mean the distance, in number of nucleotides, between the primary TATA motif and the start of transcription.

Transformation: Examples of means by which this can be accomplished are described below and include *Agrobacterium*-mediated transformation (of dicots (9-10), of monocots (11-13), and biolistic methods (14)), electroporation, in planta techniques, and the like. Such a plant containing the exogenous nucleic acid is referred to here as a $T_0$ for the primary transgenic plant and $T_1$ for the first generation.

$T_0$: As used in the current application, the term "$T_0$" refers to the whole plant, explant or callus tissue inoculated with the transformation medium and used to generate all events for a particular nucleotide sequence.

$T_1$: As used in the current application, the term $T_1$ refers to a unique event which is either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. T$_3$ progeny are the result of self-fertilization or cross pollination of a T$_2$ plant.

2. Introduction

The polynucleotides of the invention comprise root active promoters that are capable of modulating transcription in response to developmental or varying soil conditions, thereby enhancing the ability of a plant to grow under such conditions.

Such root active promoters can be used in combination with native or heterologous promoter fragments, control elements or other regulatory sequences to modulate transcription and/or translation.

Specifically, root active promoters of the invention can be used to modulate transcription of a desired polynucleotide, which include without limitation:
(a) antisense;
(b) RNAi
(c) ribozymes;
(d) coding sequences; or
(e) fragments thereof.

The root active promoter also can modulate transcription in a host genome in cis- or in trans-.

In an organism such as a plant, the root active promoters of the instant invention are useful to produce preferential transcription which results in a desired pattern of transcript levels in a particular cell, tissue or organ, or under particular conditions.

3. Description of the Invention. Experimental Procedures and Results.

A. Identifying and Isolating Promoter Sequences of the Invention

The root active promoters of the present invention are presented in Table 1 (SEQ ID NOs: 1-7). Additional promoter sequences encompassed by the invention can be identified as described below.

The effects of substitutions, insertions and deletions to the root active promoter sequences may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Cloning Methods

Isolation from genomic libraries of polynucleotides comprising the sequences of the root active promoters of the present invention is possible using known techniques.

For example, polymerase chain reaction (PCR) can amplify the desired polynucleotides using primers designed from sequences in the row titled "The spatial expression of the promoter-marker-vector". Polynucleotide libraries comprising genomic sequences can be constructed according to Sambrook et al. (1989) In Molecular Cloning: A Laboratory Manual, 2$^{nd}$ Ed. Cold Spring Harbor Press, Cold Spring Harbor, N.Y., which is hereby incorporated by reference in its entirety, for example.

Other procedures for isolating polynucleotides comprising the root active promoters sequences of the invention include, without limitation, tail-PCR and 5' rapid amplification of cDNA ends (RACE). See, for tail-PCR, for example, Liu et al. (1995 Plant J 8(3): 457-463); Liu et al. (1995) Genomics 25: 674-681; Liu et al. (1993) Nucl. Acids Res. 21(14): 3333-3334; and Zoe et al. (1999) BioTechniques 27(2): 240-24; for RACE, see, for example, PCR Protocols: A Guide to Methods and Applications, (1990) Academic Press, Inc. These publications are hereby incorporated by reference in their entirety.

(2) Chemical Synthesis

In addition, the root active promoters of the invention can be chemically synthesized according to techniques in common use. See, for example, Beaucage et al. (1981) Tet Lett 22: 1859 and U.S. Pat. No. 4,668,777.

Such chemical oligonucleotide synthesis can be carried out using commercially available devices, such as a Biosearch 4600 or 8600 DNA synthesizer (Applied Biosystems, a division of Perkin-Elmer Corp., Foster City, Calif., USA) and an Expedite (Perceptive Biosystems, Framingham, Mass., USA).

Synthetic RNA, including natural and/or analog building blocks, can be synthesized on the Biosearch 8600 machines, see above.

Oligonucleotides can be synthesized and then ligated together to construct the desired polynucleotide.

B. Isolating Functionally Similar Promoters

Included in the present invention are root active promoters exhibiting nucleotide sequence identity to those described in Table 1 (SEQ ID NOs: 1-7).

Naturally occurring root active functionally similar promoters that exhibit nucleotide sequence identity to those shown in Table 1 (SEQ ID NOs: 1-7) can be isolated using the techniques as described above. More specifically, such promoters can be identified by varying stringencies, as defined above, in typical hybridization procedures such as Southern blots or probing of polynucleotide libraries, for example.

Naturally occurring root active functionally similar promoters that do not exhibit nucleotide sequence identity to those shown in Table 1 (SEQ ID NOs: 1-7) can be isolated using the techniques as described above. More specifically, functional homologs are identified and their expression patterns compared to identify functional homologs with similar expression patterns. The promoters from these functional homologs can then be isolated as described above.

Non-natural root active promoter variants of those shown in Table 1 (SEQ ID NOs: 1-7) can be constructed using cloning methods that incorporate the desired nucleotide variation. See, for example, Ho et al. (1989) Gene 77:51-59, describing a procedure site directed mutagenesis using PCR.

C. Testing of Polynucleotides

Polynucleotides of the invention are tested for activity by cloning the sequence into an appropriate vector, transforming plants with the construct and assaying for marker gene expression. Recombinant DNA constructs are prepared which comprise the polynucleotide sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by
(a) BAC: Shizuya et al. (1992) Proc. Natl. Acad. Sci. USA 89: 8794-8797; Hamilton et al. (1996) Proc. Natl. Acad. Sci. USA 93: 9975-9979;
(b) YAC: Burke et al. (1987) Science 236:806-812;

(c) PAC: Sternberg et al. (1990) Proc Natl Acad Sci USA. January;87(1):103-7;
(d) Bacteria-Yeast Shuttle Vectors: Bradshaw et al. (1995) Nucl Acids Res 23: 4850-4856;
(e) Lambda Phage Vectors: Replacement Vector, e.g., Frischauf et al. (1983) J. Mol Biol 170: 827-842; or Insertion vector, e.g., Huynh et al. (1985) In DNA Cloning: A practical Approach, Vol. 1, Glover ed., Oxford: IRL Press: T-DNA gene fusion vectors: Walden et al. (1990) Mol Cell Biol 1: 175-194; and
(g) Plasmid vectors: Sambrook et al., infra.

Typically, the construct comprises a vector containing a sequence of the present invention operably linked to any marker gene. The polynucleotide is identified as a root active promoter by the expression of the marker gene under appropriate conditions. Many marker genes can be used including Green Fluorescent Protein (GFP), GUS, YFP, etc. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron, glyphosate or phosphinotricin. Vectors can also include origins of replication, scaffold attachment regions (SARs), markers, homologous sequences, introns, etc.

A general description of expression vectors and reporter genes can be found in Gruber, et al. (1993) Vectors for Plant Transformation In Methods in Plant Molecular Biology & Biotechnology, pp. 89-119, Glich et al. eds., CRC Press. Moreover GUS expression vectors and GUS gene cassettes are available from Clonetech Laboratories, Inc. (Palo Alto, Calif.) while luciferase expression vectors and luciferase gene cassettes are available from Promega Corp. (Madison, Wis.). GFP vectors are available from Aurora Biosciences.

D. Constructing Promoters with Control Elements (1) Combining Promoters and Promoter Control Elements The root active promoter sequences of the present invention, can be combined with each other to produce the desired preferential transcription. Also, the polynucleotides of the invention can be combined with other known sequences to obtain other useful promoters to modulate, for example, tissue specific transcription or transcription specific to certain conditions. Such preferential transcription can be determined using the techniques or assays described above.

Fragments and variants, as well as the full-length sequences of those shown in Table 1 (SEQ ID NOs: 1-7) and relatives are useful alone or in combination.

It may also be useful to attach a marker sequence to the present root active promoter in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al. (1985) Nature 317: 741-744; Gordon-Kamm et al. (1990) Plant Cell 2: 603-618; and Stalker et al. (1988) Science 242: 419-423). Other marker genes exist which provide hormone responsiveness.

(2) Modification of Transcription by Root Active Promoters

The root active promoters of the present invention are operably linked to a polynucleotide to be transcribed. In this manner, the root active promoter modifies transcription by modulating transcript levels of that polynucleotide when inserted into a genome.

However, prior to insertion into a genome, the root active promoter need not be linked, operably or otherwise, to a polynucleotide to be transcribed. For example, the root active promoter is inserted alone into the genome in front of a polynucleotide already present in the genome. In this manner, the root active promoter modulates the transcription of a polynucleotide that was already present in the genome. This polynucleotide may be native to the genome or inserted at an earlier time.

Alternatively, the root active promoter is inserted into a genome alone to modulate transcription. See, for example, Vaucheret et al. (1998) Plant J 16: 651-659. Rather, the root active promoter is simply inserted into a genome or maintained extrachromosomally as a way to divert transcription resources of the system to itself. This approach may be used to down-regulate the transcript levels of a group of polynucleotides.

(3) Polynucleotide to be Transcribed

The nature of the polynucleotide to be transcribed is not limited. Specifically, the polynucleotide includes sequences that have activity as RNA as well as sequences that result in a polypeptide product. These sequences include, but are not limited to, antisense sequences, RNAi sequences, ribozyme sequences, spliceosomes, amino acid coding sequences and fragments thereof.

Specific coding sequences may include, but are not limited to endogenous proteins or fragments thereof, or heterologous proteins including marker genes or fragments thereof.

Root active parameters of the present invention are useful for modulating metabolic or catabolic processes. Such processes include, but are not limited to, secondary product metabolism, amino acid synthesis, pest defense and nitrogen use. Some examples of genes, transcripts and peptides or polypeptides participating in these processes, which can be modulated by the present invention: are tryptophan decarboxylase (tdc) and strictosidine synthase (strl), dihydrodipicolinate synthase (DHDPS) and aspartate kinase (AK), ricinoleate and 3-ketoacyl-ACP synthase (KAS), *Bacillus thuringiensis* (Bt) insecticidal protein, cowpea trypsin inhibitor (CpTI), asparagine synthetase and nitrite reductase. Alternatively, expression constructs are used to inhibit expression of these peptides and polypeptides by incorporating the root active promoters in constructs for antisense use, co-suppression use or for the production of dominant negative mutations.

E. Insertion of Polynucleotide and Vectors into A Host Cell

The polynucleotides according to the present invention can be inserted into a host cell. A host cell includes but is not limited to a plant, mammalian, insect, yeast and prokaryotic cell, preferably a plant cell.

The method of insertion into the host cell genome is chosen based on convenience. For example, the insertion into the host cell genome may be accomplished either by vectors that integrate into the host cell genome or by vectors which exist independent of the host cell genome (1) Polynucleotides Autonomous of the Host Genome The polynucleotides of the present invention exist autonomously or independent of the host cell genome. Vectors of these types are known in the art and include, for example, certain types of non-integrating viral vectors, autonomously replicating plasmids, artificial chromosomes and the like.

Additionally, in some cases transient expression of a polynucleotide is desired.

(2) Polynucleotides Integrated into the Host Genome

The root active promoters of the present invention may be transformed into host cells. These transformations may be into protoplasts or intact tissues or isolated cells. Preferably expression vectors are introduced into intact tissue. General methods of culturing plant tissues are provided for example by Maki et al. (1993) Procedures for Introducing Foreign DNA into Plants In Methods in Plant Molecular Biology & Biotechnology, pp. 67-88, Glich et al. eds., CRC Press CRC; and by Phillips et al. (1988) Cell-Tissue Culture and In-Vitro Manipulation In Corn & Corn Improvement, 3rd Edition 10, pp. 345-387, Sprague et al. eds, American Society of Agronomy Inc.

Methods of introducing polynucleotides into plant tissue include the direct infection or co-cultivation of a plant cell with *Agrobacterium tumefaciens* (Horsch et al. (1985) Science 227:1229). Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al. (1995) Direct DNA transfer into intact plant cells via microprojectile bombardment In Plant Cell, Tissue and Organ Culture: Fundamental Methods, Gamborg and Phillips eds., Springer Verlag, Berlin.

In another embodiment of the current invention, expression constructs are used for gene expression in callus culture for the purpose of expressing marker genes encoding peptides or polypeptides that allow identification of transformed plants. Here, a root active promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells are transferred to callus shoot-inducing or callus root-inducing media. Gene expression occurs in the callus cells developing on the appropriate media: callus root-inducing promoters will be activated on callus root-inducing media, etc.

Examples of such peptides or polypeptides useful as transformation markers include, but are not limited to, barstar, glyphosate, chloramphenicol acetyltransferase (CAT), kanamycin, spectinomycin, streptomycin or other antibiotic resistance enzymes, green fluorescent protein (GFP), β-glucuronidase (GUS), etc. Some of the exemplary root active promoters of Table 1 (SEQ ID NOs: 1-7) will also be capable of sustaining expression in some tissues or organs after the initiation or completion of regeneration. Examples of these tissues or organs are somatic embryos, cotyledon, hypocotyl, epicotyl, leaf, stems roots, flowers and seed.

Integration into the host cell genome also can be accomplished by methods known in the art, for example, by the homologous sequences or T-DNA discussed above or using the cre-lox system (Vergunst et al. (1998) Plant Mol. Biol. 38:393).

F. Using the Promoters of the Invention (1) Common Uses

In yet another embodiment, the root active promoters of the present invention are used to further understand developmental mechanisms. For example, root active promoters that are specifically induced during callus, somatic embryo, shoot or root formation are used to explore the effects of overexpression, repression or ectopic expression of target genes or for isolation of trans-acting factors.

The vectors of the invention are used not only for expressing coding regions, but also in exon-trap cloning or promoter trap procedures to detect differential gene expression in various tissues (Lindsey et al. (1993) Transgenic Research 2:3347; Auch & Reth, et al. Nucleic Acids Research 18(22): 674, Nov. 25, 1990).

Entrapment vectors, first described for use in bacteria (Casadaban and Cohen (1979) Proc Nat Aca Sci USA 76: 4530; Casadaban et al. (1980) J. Bacteriol 143: 971) permit selection of insertional events that lie within coding sequences. Entrapment vectors are introduced into pluripotent ES cells in culture and then passed into the germline via chimeras (Gossler et al. (1989) Science 244: 463; Skarnes (1990) Biotechnology 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, constitutively active constructs can be eliminated by screening only bacteria that do not express the reporter gene under laboratory conditions. The bacteria selected by such a method contain constructs that are selectively induced only during infection of the host. The IVET approach can be modified for use in plants to identify genes induced in either the bacteria or the plant cells upon pathogen infection or root colonization. For information on IVET see the articles by Mahan et al. (1993) in Science 259:686-688, Mahan et al. (1995) in PNAS USA 92:669-673, Heithoff et al. (1997) in PNAS USA 94:934-939 and Wang et al. (1996) in PNAS USA. 93:10434.

(2) Particular Uses

Nutrient availability is arguably the rate-limiting element in plant growth and all field crops have a fundamental dependence on exogenous nutrient sources to a greater or lesser degree. Increased efficiency of nutrient use by plants enables the production of higher yields with existing fertilizer inputs and/or enables existing yields of crops to be obtained with lower fertilizer input or enables better yields on soils of poorer quality. Also, higher amounts of proteins in the crops are produced more cost-effectively.

Root active promoter sequences are used in combination with gene coding sequences, either gDNA or cDNA, to induce the expression of proteins and enzymes during conditions of low soil or solution nutrient concentration. Increased mRNA expression via one of the root active promoters described herein is used to overcome rate limiting steps in nutrient assimilation, transport and metabolism. General reviews of some of these processes can be found in: Derlot. et al. (2001) Amino Acid Transport In Plant Nitrogen, pp. 167-212, Lea and Morot-Gaudry eds., Springer-Verlag, Berlin, Heidelberg; Glass et al. (2002) J. Exp. Bot. 53: 855-864, Krapp et al. (2002) Nitrogen and Signaling. In Photosynthetic Nitrogen Assimilation and Associated Carbon Respiratory Metabolism, pp. 205-225, Foyer and Noctor eds., Kluwer Academic Publisher, Dordrecht, The Netherlands; and Touraine et al. (2001) Nitrate uptake and its regulation. In Plant Nitrogen, pp. 1-36, Lea and Morot-Gaudry eds, Springer-Verlag, Berlin, Heidelberg.

In addition, approximately eighty percent of the terrestrial plants are involved in a symbiotic relationship with arbuscular-mychorrhizal (AM) fungi. This symbiosis is primarily advantageous for the plant when phosphate or zinc availability is limited. Here, the AM fungal hyphae in soil areas distant from the root surface take up nutrients and transport them via symbiotic structures with in the root cortex to the vascular region (see Smith and Read (1997) In:Mycorrhizal Symbiosis, Academic Press, San Diego, Calif.). Proteins contributing to cell wall structure are involved in alterations in the extracellular matrix of the plant's cortical cells following colonization by AM fungi. Overexpression of the genes generating such proteins allow more efficient nutrient uptake, decreasing the need for externally applied fertilizers.

The promoter of the invention can be used to modulate transcription of a polynucleotide to confer desired characteristics to a plant. The polynucleotides to be so modulated can be:

(a) polynucleotides that confer resistance or tolerance to insects, nematodes, fungi, bacteria, viruses, seed as those that code for *Bacillus thuringiensis* (Bt) insecticidal protein;

(b) polynucleotides that confer increased biomass, higher seed yield, reduced nitrogen seeds, faster rate of growth or faster seedling growth, such as those described in co-pending application Ser. No. 11/298,391, filed on Dec. 8, 2005 entitled "Nucleotide Sequences and Corresponding Polypeptides Conferring Modulated Plant Size and Biomass in Plants"; and (c) polynucleotides that confer enhanced composition to plants, such as those described in co-pending U.S. Application Ser. No. 60/730,079 and 60/722,708 filed on Oct. 25, 2005 and Sep. 30, 2005, respectively.

Root active promoters are also used to turn off the expression of genes that are not beneficial to root development and nutrient uptake, use and/or transport. Here, the root active promoter is operably linked to the antisense orientation of a non-beneficial gene sequence. Expression of this antisense gene sequence has the effect of decreasing the amount of the non-beneficial sequence such that the expression of the protein encoded by the non-beneficial sequence is reduced. The reduction in expression of the non-beneficial sequence leads to a reduction in the genetic function of the protein, thus allowing for more efficient development and nutrient uptake, utilization and transport (Hamada et al. (1996) Transgenic Res 5: 115-121; Takahashi et al. (2001) Plant Physiol. 126: 731-741; Temple et al. (1998) Plant Mol Biol 37: 535-547).

Root active promoters are further used to express a non-beneficial sequence in inverted orientation, thus producing a double stranded RNA molecule. Double stranded RNAs are recognized in plant cells as foreign and are targeted for degradation (Vance and Vaucheret (2001) Science 292: 2277-2280; Wesley et al. (2001) Plant J 27: 581-590.). The end result is reduced expression of the mRNA of the non-beneficial sequence, which leads to reduced gene function (Tang et al. (2003) Genes Dev 17: 49-63).

Another alternative consists in utilizing the promoters of the invention to inhibit expression of a root active polypeptide in a plant species of interest. The term "expression" refers to the process of converting genetic information encoded in a polynucleotide into RNA through transcription of the polynucleotide (i.e., via the enzymatic action of an RNA polymerase), and into protein, through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a root active polypeptide. A nucleic acid that decreases the level of a transcription or translation product of a gene encoding a root active polypeptide is transcribed into an antisense nucleic acid similar or identical to the sense coding sequence of the root active polypeptide. Alternatively, the transcription product of an isolated nucleic acid can be similar or identical to the sense coding sequence of a root active polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the root active polypeptide of interest, and can have a length that is shorter, the same as, or longer than the corresponding length of sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., 1996, *Bioorgan. Med. Chem.*, 4: 5-23. In addition, the deoxyphosphate backbone can be replaced with, for example, a phosphorothioate or phosphorodithioate backbone, a phosphoroamidite, or an alkyl phosphotriester backbone.

Root active promoters that are expressed in the root are used to modify root architecture by increasing or decreasing the expression of genes involved in primary and lateral root formation. For example the ANR1 gene is involved in nitrogen dependent lateral root formation (Zhang and Forde (2000) J. Exp. Bot 51: 51-59). Antisense inhibition of ANR1 gene expression results in a decrease in lateral root formation at inducing concentrations of nitrate (Zhang and Forde (1998) Science 279: 407-409.). Conversely, increased expression of ANR1 and other proteins involved in lateral root formation are used to increase lateral root number and length and thus increase nitrogen uptake from the soil or solution by increasing surface area contact between soil or solution and root absorbing surface.

The root active promoters of the present invention are also useful for modulating uptake, use and metabolism of other nutrients. For example, the Sultr1 gene is a sulfate transporter while ADT1 is a potassium channel. The promoters of the invention are used to increase the expression of these gene products. These gene products modify the response of the plant to available sulfer and potassium.

The root active promoters of the invention also down-regulate genes which lead to feedback inhibition, for example of nitrogen uptake and reduction. An example of such genes are those encoding the 14-3-3 proteins, which repress nitrate reductase (Swiedrych et al. (2002) J Agric Food Chem 27;50(7):2137-41. Here, the root active promoters described herein are used to drive expression of an antisense copy of a 14-3-3 protein. The resulting transgenic plants have an increase in amino acid content and protein content in the seed and/or leaves. Such plants are especially useful for livestock feed. For example, an increase in amino acid and/or protein content in alfalfa provides an increase in forage quality and thus enhanced nutrition.

I. Experimental Procedures and Results

GFP Experimental Procedures and Results

Procedures

The polynucleotide sequences of the present invention are tested for promoter activity using Green Fluorescent Protein (GFP) assays in the following manner.

Approximately 1-2 kb of genomic sequence occurring immediately upstream of the ATG translational start site of the gene of interest is isolated using appropriate primers tailed with BstXI restriction sites. Standard PCR reactions using these primers and genomic DNA are conducted. The resulting product is isolated, cleaved with BstXI and cloned into the BstXI site of an appropriate vector.

Transformation

The following procedure is used for transformation of plants

1. Seed Preparation and Plant Growth.

A homogeneous mixture of *Arabidopsis thaliana* seed in a 0.2% Phytagar solution is inclubated at 4° C. in the dark for 3 days. Seed is planted in 4 inch pots in a soil miture of Sunshine Mix, Vermiculite, Marathon and Osmocote. Pots are placed in flats, covered with plastic domes and subsequently subirrigated. After 3 to 4 days, the domes are removed.

Seven to ten days after planting, seedlings are thinned to 20 plants per pot. When 5-10 cm long bolts appear, they are clipped between the first node and the stem base to induce secondary bolts. Six to 7 days after clipping, the plants are transformed via dipping infiltration.

2. Preparation of *Agrobacterium*.

Each 4 inch pot is inverted and the aerial portion of the plants submerged into a 16 oz. polypropylene container holding 200 mls of *Agrobacterium tumefaciens* ($1\times10^7$ bacteria) in Infiltration media (2.2 g MS salts, 50 g sucrose, 110 µg BAP and 0.02% Silwet L-77 per liter). After 5 minutes, the *Agrobacterium* solution is removed while keeping the polypropylene container in place and the pots returned to an upright position. Pots are then placed in flats (10 pots per flat) containing approximately 1 inch of water and covered with shade cloth. After 24 hours, the shade cloth and polypropylene containers are removed.

After flowering, each pot is covered with a ciber plant sleeve. When plants are completely dry, seed is collected and stored.

3. High Throughput Screening—T1 Generation

Transformed seed are placed in pots containing a water saturated soil miture of Sunshine Mix, Vermiculite, Marathon and Osmocote. Pots are then placed in flats and stored in the dark at 4° C. for at least 2 days. After transferring the flats from the cooler to the greenhouse, they are covered with 55% shade cloth and propagation domes. When the cotyledons are fully expanded the cloth and domes are removed.

Plants are sprayed with a solution of 3 ml concentrated Finale in 48 oz water. Spraying is repeated every 3-4 days until only transformants remain. Transformants are thinned to a maximum of 5 plants per pot.

4. GFP Assay

Tissues are dissected by eye or under magnification using INOX 5 grade forceps and placed on a slide with water and coverslip. An attempt is made to record images of observed expression patterns at earliest and latest stages of development of tissues listed below. Specific tissues will be preceded with High (H), Medium (M), Low (L) designations.

T3 Seedling: This is done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in PowerPoint specifying organ and specific expressing tissues.

Instrumentation:

An Inverted Leica DM IRB microscope is used with two Fluorescence filter blocks: (1) Blue excitation BP 450-490; long pass emission LP 515 and (2) Green excitation BP 515-560; long pass emission LP 590. The following objec-

| | |
|---|---|
| Flower | Pedicel, receptacle, nectary, sepal, petal, filament, anther, pollen, carpel, style, papillae, vascular, epidermis, stomata, trichome |
| Silique | Stigma, style, carpel, septum, placentae, transmitting tissue, vascular, epidermis, stomata, abscission zone, ovule |
| Ovule | Pre-fertilization: inner integument, outer integument, embryo sac, funiculus, chalaza, micropyle, gametophyte<br>Post-fertilization: zygote, inner integument, outer integument, seed coat, primordial, chalaza, miccropyle, early endosperm, mature endosperm, embryo |
| Embryo | Suspensor, preglobular, globular, heart, torpedo, late, mature, provascular, hypophysis, radicle, cotyledons, hypocotyl |
| Stem | Epidermis, cortex, vascular, xylem, phloem, pith, stomata, trichome |
| Leaf | Petiole, mesophyll, vascular, epidermis, trichome, primordial, stomata, stipule, margin |

T1 Mature: These are the T1 plants resulting from independent transformation events. These are screened between stage 6.50-6.90 (means the plant is flowering and that 50-90% of the flowers that the plant will make have developed) which is 4-6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal microscopy.

T2 Seedling: Progeny are collected from the T1 plants giving the same expression pattern and the progeny (T2) are sterilized and plated on agar-solidified medium containing M&S salts. In the event that there is no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings are screened until two seedlings are observed to have the same pattern. Generally found the same expression pattern is found in the first two seedlings. However, up to 6 seedlings are screened before "no expression pattern" is recorded. All constructs are screened as T2 seedlings even if they did not have an expression pattern in the T1 generation.

T2 Mature: The T2 mature plants are screened in a similar manner to the T1 plants. The T2 seeds are planted in the greenhouse, exposed to selection and at least one plant screened to confirm the T1 expression pattern. In instances where there are any subtle changes in expression, multiple plants are examined and the changes noted in the tables.

tives are used: HC PL FLUOTAR 5X/0.5, HCPL APO 10X/0.4 IMM water/glycerol/oil, HCPL APO 20X/0.7 IMM water/glycerol/oil and HCXL APO 63X/1.2 IMM water/glycerol/oil. A Leica TCS SP2 confocal scanner with a Spectral range of detector optics of 400-850 nm was used with a variable computer controlled pinhole diameter, an Optical zoom 1-32× and four simultaneous detectors: three channels for collection of fluorescence or reflected light and one channel for transmitted light detector. The laser sources are: (1) Blue Ar 458/5 mW, 476 nm/5 mW, 488 nm/20 mW, 514 nm/20 mW, (2) Green HeNe 543 nm/1.2 mW and (3) Red HeNe 633 nm/10 mW.

Confirmation of promoter sequence: Promoter construct sequence is 5' verified in T1 mature plants and confirmed in the following generation by 5' and 3' sequencing of the entire promoter of two or 3 events. Sequences from all events are used to generate a consensus sequence. In every case, the sequences of the 2-3 events are matched.

Table 1

Table 1 includes various information about each root active promoter of the invention including the spatial expression promoted by each promoter, and the corresponding results from different expression experiments. The sequences for each promoter is set forth in the Sequence Listing.

Table 1 consists of the Promoter Reports for each root active promoter of the invention and provides details for expression driven by each of the nucleic acid root active promoter sequences as observed in transgenic plants. The results are presented as summaries of the spatial expression, which provide information as to gross and/or specific expression in various plant organs and tissues. The observe expression pattern is also resented, which gives details of expression during different generations or different developmental stages within a generation. Additional information is provided regarding the associated gene, the GenBank reference, the source organism of the promoter, and the vector and marker genes used for the construct used to produce the transgenic plant. The following symbols are used consistently throughout the Table:

T1: First generation transformant
T2: Second generation transformant
T3: Third generation transformant
(L): low expression level
(M): medium expression level
(H): high expression level

TABLE 1

Promoter Expression Report #239
Promoter Tested In: *Arabidopsis thaliana*, Wassilewskija (WS) ecotype
Spatial expression summary:

| | |
|---|---|
| Flower | H nectary H anther H pollen H H style H silique |
| Silique | H style H carpel H septum |
| Ovule | Post-fertilization: H zygote H suspensor H seed coat H embryo |
| Embryo | H suspensor H globular H heart H torpedo H late H mature H radicle H cotyledons |
| Stem | H vascular H xylem H phloem H pith H interfascicular |
| Leaf | H vascular H epidermis |
| Hypocotyl | M epidermis M vascular |
| Cotyledon | M vascular M epidermis |
| Rosette Leaf | M vascular H epidermis H primordia |
| Primary Root | L cortex H vascular H quiescent H root cap |
| Lateral root | H epidermis H initials H flanking cells H lateral root cap |

Observed expression pattern:
T1 mature: High expression throughout all aerial tissues of the mature plant. In the flower, GFP is expressed in nectary glands, anther and silique. GFP expression encompasses sporogenic and tapetum cell types within the locules of developing anthers and pollen of mature anthers. GFP expressed throughout carples, ovules and embryos of siliques. No expression observed in placenta. High expression throughout early and mature embryos. High GFP expression throughout the suspensor apparatus shows a unique developmental aspect of embryogenesis. Ovule and funiculus junction appears where the suspensor is attached to funiculus.
GFP is expressed in epidermis and vasculature of leaf. No mesophyll expression detected. GFP expressed throughout vascular and ground cells of inner stem.
T2 seedling: Expressed throughout aerial tissues of seedlings. Highest GFP expression in epidermis of emerging rosette leaves and cotyledons decreasing in hypocotyl toward root transition zone. Vascular expression throughout seedling. Weak root epidermal expression.

| | |
|---|---|
| Expected expression pattern: | Roots - Mixed exp loud in roots |
| Selection Criteria: | Microarray |
| Gene: | Meprin and TRAF homology domain-containing protein/MATH domain |
| GenBank: | NM_122529 *Arabidopsis thaliana* meprin and TRAF homology domain-containing protein/MATH domain-containing protein (At5g26280) mRNA, complete cds gi|18421008| |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling  T2 Mature  T3 Seedling |
| T1 Mature Plant Expression | Organs/Tissues screened |
| Events Screened: n = 3 | Events Expressing: n = 3 |

GFP Expression Detected

| | |
|---|---|
| X Flower | pedicel receptacle H nectary sepal petal filament H anther H pollen H carpel H style papillae vascular epidermis stomata trichome H silique |
| X Silique | stigma H style H carpel H septum placentae funiculus transmitting tissue vascular epidermis stomata abscission zone ovule |
| X Ovule | Pre-fertilization: primordia inner integument outer integument embryo sac funiculus chalaza micropyle gametophyte Post-fertilization: H zygote H suspensor embryo sack funiculus inner integument outer integument endothelium H seed coat primordia chalaza micropyle early endosperm mature endosperm H embryo |
| X Embryo | H suspensor preglobular H globular H heart H torpedo H late H mature provascular hypophysis H radicle H cotyledons |
| X Stem | epidermis cortex H interfascicular region H vascular H xylem H phloem H pith stomata trichome |
| X Leaf | petiole mesophyll H vascular H epidermis trichome primordia stomata stipule margin |
| Shoot apical meristem | Shoot apical meristem Flower primordium |

Chalaza (Ch), Epidermis (Ep), Carpel (Ca), Embryo (Em), Funiculus (Fn), Interfascicular region (Ifr), Micropyle (Mp), Nectary (Ne), Ovule (Ov), Phloem (Ph), Pith (Pi), Pollen (Po), Seed coat (Sc), Sepal (Se), Septum (Sp), Stigma (Sg), Style (Sy), Suspensor (Su), Suspensor apparatus (Sa), Root meristem (Rm), Vascular (Vs), Xylem (Xy)

| | |
|---|---|
| T2 Seedling Expression | Tissues Screened |
| Events Screened: n = 3 | Events Expressing: n = 3 |

Seedlings expressing/Seedlings screened

TABLE 1-continued

Event-01: 3/5
Event-02: 4/6
Event-03: 3/6
GFP Expression Detected
| | |
|---|---|
| X Hypocotyl | M epidermis cortex M vascular xylem phloem stomata |
| X Cotyledon | mesophyll M vascular M epidermis margin petiole stomata hydathode |
| X Rosette Leaf | mesophyll M vascular H epidermis trichome petiole H primordia stomata stipule margin hydathode |
| X Primary Root | epidermis trichoblast atrichoblast L cortex endodermis H vascular xylem phloem pericycle H quiescent columella H root cap root hairs |
| X Lateral root | H epidermis trichoblast atrichoblast cortex endodermis H initials H flanking cells vascular H lateral root cap |
| Shoot apical meristem | Shoot apical meristem |

Cortex (Cr), Cotyledon (Co), Epidermis (Ep), Hypocotyl (Hy), Lateral root (Lr), Pericycle (Pr), Quiescent center (Qc), Root (Rt), Vascular (Vs)
Construct: PT0839 (SEQ ID NO. 1)
Promoter candidate I.D: 15372166
cDNA I.D: 23546458
Lines expressing: PT0839-01, -02, -03
Promoter Expression Report #243
Promoter Tested In: *Arabidopsis thaliana*, Wassilewskija (WS) ecotype
Spatial expression summary:
Primary Root   H epidermis H trichoblast H atrichoblast H cortex H vascular H root hairs
Observed expression pattern:
T1 mature: Root specific expression in mature plant. No expression observed in aerial organs.
T2 seedling: GFP expression specific to epidermal cells, cortex, and vasculature of root. Higher GFP expression near root transition zone decreasing toward root tip. Not observed in aerial organs of seedlings.
Expected expression pattern: Roots - Up in roots only
Selection Criteria: Microarray
Gene: Expressed protein
GenBank: NM_117977 *Arabidopsis thaliana* expressed protein (At4g18610) mRNA, complete cds gi|30684471|ref|NM_117977.2|[30684471]
Source Promoter Organism: *Arabidopsis thaliana*, Columbia (Col) ecotype
Vector: pNewbin4-HAP1-GFP
Marker Type: GFP-ER
Generation Screened: XT1 Mature XT2 Seedling  T2 Mature  T3 Seedling
T1 Mature Plant Expression   Organs/Tissues screened
Events Screened: n = 3    Events Expressing: n = ≧1
Mature roots extending through drain holes in pots pulled and screened.
GFP Expression Detected
| | |
|---|---|
| Flower | pedicel receptacle nectary sepal petal filament anther pollen carpel style papillae vascular epidermis stomata trichome silique |
| Silique | stigma style carpel septum placentae funiculus transmitting tissue vascular epidermis stomata abscission zone ovule |
| Ovule | Pre-fertilization: primordia inner integument outer integument embryo sac funiculus chalaza micropyle gametophyte Post-fertilization: zygote suspensor embryo sack funiculus inner integument outer integument endothelium seed coat primordia chalaza micropyle early endosperm mature endosperm embryo |
| Embryo | suspensor preglobular globular heart torpedo late mature provascular hypophysis radicle cotyledons root meristem shoot meristem |
| Stem | epidermis cortex interfascicular region vascular xylem phloem pith stomata trichome |
| Leaf | petiole mesophyll vascular epidermis trichome primordia stomata stipule margin |
| Shoot apical meristem | shoot apical meristem flower primordium |
| X Root | M mature root |

Mature roots extending through drain holes in pots pulled and screened.
T2 Seedling Expression    Tissues Screened
Events Screened: n = 3    Events Expressing: n = 3
Seedlings expressing/Seedlings screened
Event-01: 3/5
Event-02: 4/6
Event-03: 3/5
GFP Expression Detected
| | |
|---|---|
| Hypocotyl | epidermis cortex vascular xylem phloem stomata |
| Cotyledon | mesophyll vascular epidermis margin petiole stomata hydathode |
| Rosette Leaf | mesophyll vascular epidermis trichome petiole primordia stomata stipule margin hydathode |

TABLE 1-continued

| | |
|---|---|
| X Primary Root | H epidermis H trichoblast H atrichoblast H cortex endodermis H vascular xylem phloem pericycle quiescent columella root cap H root hairs |
| Lateral root | epidermis trichoblast atrichoblast cortex endodermis initials flanking cells vascular lateral root cap |
| Shoot apical meristem | shoot apical meristem |

Cortex (Cr), Epidermis (Ep), Hypocotyl (Hy), Root (Rt), Root hair (Rh), Vasculature (Vs)
Construct: PT0758 (SEQ ID NO. 2)
Promoter candidate I.D: 15371866
cDNA I.D: 23511154
Lines expressing: PT0758-01, -02, -03
Promoter Expression Report #244
Promoter Tested In: *Arabidopsis thaliana*, Wassilewskija (WS) ecotype
Spatial expression summary:

| | |
|---|---|
| Flower | H receptacle |
| Primary Root | H epidermis H cortex |

Observed expression pattern:
T1 mature: GFP expression specific to receptacle of flowers in mature plants.
T2 seedling: GFP expressed in epidermis and cortex of roots.
Expected expression pattern: Roots - Up in roots only
Selection Criteria: Microarray
Gene: pollen Ole e 1 allergen and extensin
GenBank: NM_148700 *Arabidopsis thaliana* pollen Ole e 1 allergen and extensin family protein (At3g09925) mRNA, complete cds gi|22330939|ref|NM_148700.1|[22330939]
Source Promoter Organism: *Arabidopsis thaliana*, Columbia (Col) ecotype
Vector: pNewbin4-HAP1-GFP
Marker Type: GFP-ER
Generation Screened: X T1 Mature X T2 Seedling   T2 Mature   T3 Seedling
T1 Mature Plant Expression   Organs/Tissues screened
Events Screened: n = 2   Events Expressing: n = 2
GFP Expression Detected

| | |
|---|---|
| X Flower | pedicel H receptacle nectary sepal petal filament anther pollen carpel style papillae vascular epidermis stomata trichome silique |
| Silique | stigma style carpel septum placentae funiculus transmitting tissue vascular epidermis stomata abscission zone ovule |
| Ovule | Pre-fertilization: primordia inner integument outer integument embryo sac funiculus chalaza micropyle gametophyte Post-fertilization: zygote suspensor embryo sack funiculus inner integument outer integument endothelium seed coat primordia chalaza micropyle early endosperm mature endosperm embryo |
| Embryo | suspensor preglobular globular heart torpedo late mature provascular hypophysis radicle cotyledons root meristem shoot meristem |
| Stem | epidermis cortex interfascicular region vascular xylem phloem pith stomata trichome |
| Leaf | petiole mesophyll vascular epidermis trichome primordia stomata stipule margin |
| Shoot apical meristem | shoot apical meristem flower primordium |

Abscission zone (Az), Receptacle (Re)
T2 Seedling Expression   Tissues Screened
Events Screened: n = 3   Events Expressing: n = 3
Seedlings expressing/Seedlings screened
Event-01: 4/6
Event-02: 3/7
Event-03: 4/7
GFP Expression Detected

| | |
|---|---|
| Hypocotyl | epidermis cortex vascular xylem phloem stomata |
| Cotyledon | mesophyll vascular epidermis margin petiole stomata hydathode |
| Rosette Leaf | mesophyll vascular epidermis trichome petiole primordia stomata stipule margin hydathode |
| X Primary Root | H epidermis trichoblast atrichoblast H cortex endodermis vascular xylem phloem pericycle quiescent columella root cap root hairs |
| Lateral root | epidermis trichoblast atrichoblast cortex endodermis initials flanking cells vascular lateral root cap |
| Shoot apical meristem | shoot apical meristem |

Epidermis (Ep), Cortex (Cr), Root hair (Rh), Root (Rt)
Construct: PT0888 (SEQ ID NO. 3)
Promoter candidate I.D: 15371803
cDNA I.D: 23516453
Lines expressing: PT0888-01, -02, -03

TABLE 1-continued

```
Promoter Expression Report #248
Promoter Tested In: Arabidopsis thaliana, Wassilewskija (WS) ecotype
Spatial expression summary:
Lateral root                H endodermis H pericycle
Observed expression pattern:
T1 mature: No expression observed.
T2 seedling: GFP expression specific to pericycle and or endodermal cells of lateral roots.
Expected expression pattern:   Roots - Up in roots only
Selection Criteria:            Microarray
Gene:                          expressed protein
GenBank: NM_105702 Arabidopsis thaliana expressed protein (At1g70340) mRNA, complete
cds gi|42563106|ref|NM_105702.2|[42563106]
Source Promoter Organism:   Arabidopsis thaliana, Columbia (Col) ecotype
Vector:                     pNewbin4-HAP1-GFP
Marker Type:                GFP-ER
Generation Screened:     XT1 Mature   XT2 Seedling   T2 Mature   T3 Seedling
T1 Mature Plant Expression   Organs/Tissues screened
Events Screened:   n = 3    Events Expressing:   n = 0
No GFP Expression Detected
T2 Seedling Expression        Tissues Screened
Events Screened: n = 3        Events Expressing: n = 3
Seedlings expressing/Seedlings screened
Event-01: 4/6
Event-02: 5/6
Event-03: 3/6
GFP Expression Detected
Hypocotyl         epidermis cortex vascular xylem phloem stomata
Cotyledon         mesophyll vascular epidermis margin petiole stomata
                  hydathode
Rosette Leaf      mesophyll vascular epidermis trichome petiole
                  primordia stomata stipule margin hydathode
Primary Root      epidermis trichoblast atrichoblast cortex endodermis
                  vascular xylem phloem pericycle quiescent columella root
                  cap root hairs
X Lateral root    epidermis trichoblast atrichoblast cortex H endodermis H
                  pericycle vascular initials flanking cells lateral root cap
Shoot apical      shoot apical meristem
meristem
Endodermis (Eo), Hypocotyl (Hy), Lateral root (Lr), Pericycle (Pr)
Construct:              PT0803 (SEQ ID NO. 4)
Promoter candidate I.D:   15372073
cDNA I.D:                 23660093
Lines expressing:         PT0803-01, -02, -03
Promoter Expression Report #249
Promoter Tested In: Arabidopsis thaliana, Wassilewskija (WS) ecotype
Spatial expression summary:
Primary Root              H vascular M pericycle
Observed expression pattern:
T1 mature: No expression observed.
T2 seedling: GFP expression specific to root vasculature.
Expected expression pattern:   Roots - Up in roots only
Selection Criteria:            Microarray
Gene:                          Expressed protein
GenBank: NM_130256 Arabidopsis thaliana expressed protein (At2g46890) mRNA,
complete cds gi|30690536|ref|NM_130256.3|[30690536]
Source Promoter Organism:   Arabidopsis thaliana, Columbia (Col) ecotype
Vector:                     pNewbin4-HAP1-GFP
Marker Type:                GFP-ER
Generation Screened:     X T1 Mature X T2 Seedling   T2 Mature   T3 Seedling
T1 Mature Plant Expression   Organs/Tissues screened
Events Screened:   n = 3    Events Expressing:   n = 0
No GFP Expression Detected
T2 Seedling Expression        Tissues Screened
Events Screened: n = 3        Events Expressing: n = 3
Seedlings expressing/Seedlings screened
Event-01: 3/6
Event-02: 3/5
Event-03: 5/6
GFP Expression Detected
Hypocotyl         epidermis cortex vascular xylem phloem stomata
Cotyledon         mesophyll vascular epidermis margin petiole stomata
                  hydathode
Rosette Leaf      mesophyll vascular epidermis trichome petiole
                  primordia stomata stipule margin hydathode
X Primary Root    epidermis trichoblast atrichoblast cortex endodermis
                  H vascular xylem phloem M pericycle quiescent
                  columella root cap root hairs
Lateral root      epidermis trichoblast atrichoblast cortex endodermis
                  initials flanking cells vascular lateral root cap
```

TABLE 1-continued

Shoot apical meristem — shoot apical meristem
Hypocotyl (Hy), Pericycle (Pr), Vasculature (Vs)
Construct: PT0779 (SEQ ID NO. 5)
Promoter candidate I.D: 15371971
cDNA I.D: 23432043
Lines expressing: PT0779-01, -02, -03
Promoter Expression Report #250
Promoter Tested In: *Arabidopsis thaliana*, Wassilewskija (WS) ecotype
Spatial expression summary:
Ovule — Post-fertilization: M outer integument L seed coat
Embryo — L suspensor H torpedo H late H mature
Primary Root — H endodermis
Observed expression pattern:
T1 mature: GFP expressed in developing seed coat in developing ovules decreasing in maturing seed. High GFP expression throughout embryos.
T2 seedling: GFP expression specific to root endodermis cells.
Expected expression pattern: Root - Up in roots only
Selection Criteria: Microarray
Gene: Patatin-related
GenBank: NM_119126 *Arabidopsis thaliana* patatin-related (At4g29800) mRNA, complete cds
Source Promoter Organism: *Arabidopsis thaliana*, Columbia (Col) ecotype
Vector: pNewbin4-HAP1-GFP
Marker Type: GFP-ER
Generation Screened: X T1 Mature X T2 Seedling T2 Mature T3 Seedling
T1 Mature Plant Expression Organs/Tissues screened
Events Screened: n = 2  Events Expressing: n = 2
GFP Expression Detected
Flower — pedicel receptacle nectary sepal petal filament anther pollen carpel style papillae vascular epidermis stomata trichome silique
Silique — stigma style carpel septum placentae funiculus transmitting tissue vascular epidermis stomata abscission zone ovule
X Ovule — Pre-fertilization: primordia inner integument outer integument embryo sac funiculus chalaza micropyle gametophyte
Post-fertilization: zygote suspensor embryo sack funiculus inner integument M outer integument endothelium L seed coat primordia chalaza micropyle early endosperm mature endosperm embryo
X Embryo — L suspensor preglobular globular heart H torpedo H late H mature provascular hypophysis radicle cotyledons root meristem shoot meristem
Stem — epidermis cortex interfascicular region vascular xylem phloem pith stomata trichome
Leaf — petiole mesophyll vascular epidermis trichome primordia stomata stipule margin
Shoot apical meristem — shoot apical meristem flower primordium
Seed coat (Sc), Suspensor (Su), Root cap (Rc)
T2 Seedling Expression Tissues Screened
Events Screened: n = 2  Events Expressing: n = 2
Seedlings expressing/Seedlings screened
Event-01: 3/6
Event-02: 4/6
GFP Expression Detected
Hypocotyl — epidermis cortex vascular xylem phloem stomata
Cotyledon — mesophyll vascular epidermis margin petiole stomata hydathode
Rosette Leaf — mesophyll vascular epidermis trichome petiole primordia stomata stipule margin hydathode
X Primary Root — epidermis trichoblast atrichoblast cortex H endodermis vascular xylem phloem pericycle quiescent columella root cap root hairs
Lateral root — epidermis trichoblast atrichoblast cortex endodermis initials flanking cells vascular lateral root cap
Shoot apical meristem — shoot apical meristem
Endodermis (Eo), Hypocotyl (Hy), Root (Rt)
Construct: PT0837 (SEQ ID NO. 6)
Promoter candidate I.D: 15371899
cDNA I.D: 23522002
Lines expressing: PT0837-01, -02
Promoter Expression Report #251
Promoter Tested In: *Arabidopsis thaliana*, Wassilewskija (WS) ecotype
Spatial expression summary:
Primary Root — H epidermis H cortex M root hairs
Observed expression pattern:
T1 mature: No expression observed.

TABLE 1-continued

T2 seedling: GFP expression specific to epidermal and cortex cells of primary root. Highest
expression observed near root transition zone decreasing toward root tip. No expression
observed in aerial tissues of seedling.

| | |
|---|---|
| Expected expression pattern: | Root - Mixed exp loud in roots |
| Selection Criteria: | Microarray |
| Gene: | Cytochrome P450, CYP81F4 |
| GenBank: | NM_119904 *Arabidopsis thaliana* cytochrome P450, putative (At4g37410) mRNA, |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling   T2 Mature   T3 Seedling |
| T1 Mature Plant Expression | Organs/Tissues screened |
| Events Screened:   n = 3 | Events Expressing:   n = 0 |
| No GFP Expression Detected | |
| T2 Seedling Expression | Tissues Screened |
| Events Screened: n = 3 | Events Expressing: n = 2 |
| Seedlings expressing/Seedlings screened | |
| Event-01: 4/5 | |
| Event-02: 5/6 | |
| GFP Expression Detected | |
| Hypocotyl | epidermis cortex vascular xylem phloem stomata |
| Cotyledon | mesophyll vascular epidermis margin petiole stomata hydathode |
| Rosette Leaf | mesophyll vascular epidermis trichome petiole primordia stomata stipule margin hydathode |
| X Primary Root | H epidermis trichoblast atrichoblast H cortex endodermis vascular xylem phloem pericycle quiescent ☐columella ☐root cap M root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |
| Cortex (Cr), Epidermis (Ep), Hypocotyl (Rt), Root (Rt), Root hair (Rh) | |
| Construct: | PT0818 (SEQ ID NO: 7) |
| Promoter candidate I.D: | 15372154 |
| cDNA I.D: | 23550576 |
| Lines expressing: | PT0818-01, -02 |

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

Each of the following co-pending applications are hereby expressly incorporated by reference in its entirety: U.S. application Ser. No. 11/298,391, filed on Dec. 8, 2005 entitled "Nucleotide Sequences and Corresponding Polypeptides Conferring Modulated Plant Size and Biomass in Plants"; U.S. Application Ser. No. 60/730,079 filed on Oct. 25, 2005 and Ser. No. 60/722,708 filed on Sep. 30, 2005.

---

What is claimed is:

1. An isolated nucleic acid molecule comprising a root active promoter that drives transcription in a plant and comprises the nucleic acid sequence of SEQ ID NO: 2 operably linked to a heterologous nucleic acid sequence.

2. A vector comprising: a) a first nucleic acid sequence that has the sequence of SEQ ID NO: 2, and b) a second nucleic acid sequence, wherein said first and second nucleic acid sequences are operably linked, and wherein said first and second nucleic acid sequences are heterologous to each other.

3. A plant cell transformed with a first nucleic acid molecule having the sequence as set forth in SEQ ID NO: 2, wherein said first nucleic acid molecule is a root active promoter.

4. The plant cell according to claim 3, further comprising a second nucleic acid molecule operably linked to said first nucleic acid molecule.

5. A transgenic plant obtained from the plant cell according to claim 4.

6. A tissue obtained from the transgenic plant according to claim 5, wherein the tissue comprises said second nucleic acid molecule operably linked to said first nucleic acid molecule.

7. The transgenic plant according to claim 5, wherein said first nucleic acid molecule drives transcription of said second nucleic acid molecule in the roots of said transgenic plant, whereby the transcription of said second nucleic acid molecule causes said transgenic plant to have characteristics which are different from those of a naturally occurring plant of the same species cultivated under the same conditions.

8. An isolated nucleic acid molecule consisting of the nucleic acid sequence set forth in SEQ ID NO:2.

* * * * *